United States Patent
Oh

(10) Patent No.: US 8,569,045 B2
(45) Date of Patent: Oct. 29, 2013

(54) WATER TOXICITY DETECTING APPARATUS AND METHOD USING SULFUR PARTICLES

(75) Inventor: Sang Eun Oh, Chuncheon-si (KR)

(73) Assignee: University-Industry Cooperation Foundation, Kangwon University, Gangwon-do (KR)

( * ) Notice: Subject to any disclaimer, the term of this patent is extended or adjusted under 35 U.S.C. 154(b) by 1051 days.

(21) Appl. No.: 12/210,097

(22) Filed: Sep. 12, 2008

(65) Prior Publication Data

US 2009/0076733 A1 Mar. 19, 2009

(30) Foreign Application Priority Data

Sep. 14, 2007 (KR) .................. 10-2007-0093476

(51) Int. Cl.
*C12M 1/00* (2006.01)
*C12M 1/38* (2006.01)
*C12M 1/36* (2006.01)

(52) U.S. Cl.
USPC .................. 435/287.7; 435/283.1; 435/286.1; 702/19; 702/30

(58) Field of Classification Search
USPC .............. 435/283.1, 286.1, 287.1; 702/19, 30
See application file for complete search history.

(56) References Cited

U.S. PATENT DOCUMENTS 4,564,453 A * 1/1986 Coplot et al. ................. 210/614

OTHER PUBLICATIONS

Okochi et al "Development of an automated water toxicity biosensor . . . " Biotechnology and Bioengineering, vol. 87, No. 7, Sep. 30, 2004, 905-911.*

* cited by examiner

*Primary Examiner* — Nathan Bowers
(74) *Attorney, Agent, or Firm* — Intellectual Property Law Group LLP

(57) ABSTRACT

Provided are a water toxicity detecting apparatus and a method using sulfur particles. The water toxicity detecting apparatus using sulfur particles includes: a reaction container containing microbes, in which externally-supplied sulfur particles and oxygen are reacted to form sulfate ions by the microbes; a water sample inlet through which a water sample is flown into the reaction container; an air inlet through which an air is flown into the reaction container; a first detection unit which detects pH and electrical conductivity of the inflow water sample flown through the water sample inlet; a second detection unit which detects pH and electrical conductivity of the water sample containing the sulfate ions generated in the reaction container; a central processing unit which stores data of the ph and electrical conductivity of the inflow water sample flown through the water sample inlet, adjusts a pumping speed of a pump provided to the water sample inlet and a flow rate of the air, and compares data of the first detection unit with data of the second detection unit to determine presence of toxicity of the water sample; and an outlet through the after-toxicity-test water sample is exhausted from the reaction container.

14 Claims, 4 Drawing Sheets

WATER TOXICITY DETECTING APPARATUS AND METHOD USING SULFUR PARTICLES

CROSS-REFERENCE TO RELATED PATENT APPLICATION

This application claims the benefit of Korean Patent Application No. 10-2007-0093476, filed on Sep. 14, 2007, in the Korean Intellectual Property Office, the disclosure of which is incorporated herein in its entirety by reference.

BACKGROUND OF THE INVENTION

1. Field of the Invention

The present invention relates to water toxicity detecting apparatus and method using sulfur particles, and more particularly, to biological water toxicity detecting apparatus and method capable of monitoring toxicity of a water such as a river water, a waste water, and a water supply source by using obligately autotrophic microbes or some facultatively autotrophic microbes in a reaction container containing sulfur particles (electron donors) and oxygen (electron acceptors).

2. Description of the Related Art

Recently, water which is essential to all living beings has been contaminated with various toxic substances. The pollution of water seriously affects human beings' living. As the toxic substances are flown into a river or the like, water cannot be safely used as a drinking water. Therefore, in this case, very rapid emergency measures are needed.

AS the pollution of water become serious in the world, in order to protect water environment, techniques for measuring water pollution have been developed and a large amount of cost has been paid for waste water disposal in many countries.

Particularly, water pollution accidents in which toxic chemical substances are flown into an ecosystem such as a river have frequently occurred, so that the ecosystem may be polluted. Since the water pollution accidents lead to irrecoverable damages, it is important to prevent the accident in advance.

Conventionally, water living things such as water flea and fish have been used to detect the water toxic substance. In the method, a casualty of the living things due to the toxic substances is calculated. The method has a problem in that a long time is taken to detect the toxic substances.

Therefore, in addition to the method of detecting water toxicity by using only the water living things, there is a need for a new method of effectively detecting water toxicity by using other substances.

SUMMARY OF THE INVENTION

The present invention is to provide water toxicity detecting apparatus and method capable of monitoring toxicity of a water such as a river water, a waste water, and a water supply source by using obligately autotrophic microbes or some facultatively autotrophic microbes in a reaction container containing sulfur particles (electron donors) and oxygen (electron acceptors).

The present invention is not limited to the above objects, but others can be understood from the following description by the ordinarily skilled in the art.

According to an aspect of the present invention, there is provided a water toxicity detecting apparatus using sulfur particles comprising: a reaction container containing microbes, in which externally-supplied sulfur particles and oxygen are reacted to form sulfate ions by the microbes; a water sample inlet through which a water sample is flown into the reaction container; an air inlet through which an air is flown into the reaction container; a first detection unit which detects pH and electrical conductivity of the inflow water sample flown through the water sample inlet; a second detection unit which detects pH and electrical conductivity of the water sample containing the sulfate ions generated in the reaction and electrical conductivity of the inflow water sample flown through the water sample inlet, adjusts a pumping speed of a pump provided to the water sample inlet and a flow rate of the air, and compares data of the first detection unit with data of the second detection unit to determine presence of toxicity of the water sample; and an outlet through the after-toxicity-test water sample is exhausted from the reaction container.

In the above aspect, the water toxicity detecting apparatus further may comprise: a thermostat unit which maintain the reaction container at a constant temperature; an alarm unit which issues alarm when a detected value of the electrical conductivity in the reaction container deviates from a reference value; and a water sampling unit which samples the water for accurate analysis at the same time of the issuing of alarm and stores the sample.

In addition, the reaction container may be of a continuous type or a batch type.

In addition, the water toxicity detecting apparatus further may comprise a pump which is provided to the water sample inlet to introduce a river water.

In addition, the microbes may belong to the genus *Thiobacillus*.

In addition, the microbes of the genus *Thiobacillus* may be obligately autotrophic microbes or facultatively autotrophic microbes.

In addition, the obligately autotrophic microbes of the genus *Thiobacillus* may be one type of species selected from *Thiobacillus ferrooxidans*, *Thiobacillus albertis*, *Thiobacillus prosperus*, and *Thiobacillus thiooxidans* or a mixture of two or more types of species thereof.

In addition, the facultatively autotrophic microbes of the genus *Thiobacillus* may be one type of species selected from *Thiobacillus acidophilus* and *Thiobacillus cuprinus* or a mixture of two or more types of species thereof.

According to another aspect of the present invention, there is provided a water toxicity detecting method using sulfur particles, comprising: introducing the sulfur particles into a reaction container; injecting microbes into the reaction container and activating the microbes; flowing a water sample into the reaction container; supplying air to the reaction container; detecting pH and electrical conductivity of the inflow water sample flown through a water sample inlet; storing data of the pH and electrical conductivity of the inflow water sample flown through the water sample inlet and adjusting a pumping speed of a pump provided to the water sample inlet and a flow rate of the air supplied to the reaction container; and determining presence of toxicity of the water sample based on data of changes in pH and electrical conductivity between the inflow water sample flown through the water sample inlet and the water sample containing sulfate ions generated in the reaction container.

In the above aspect, the water toxicity detecting method may further comprise: comparing the detected value of electrical conductivity with a reference value and issuing alarm of abnormal water quality if the detected value is less than the reference value; and sampling the water for accurate analysis at the same time of the issuing of alarm and storing the sample.

In addition, the microbes may belong to the genus *Thiobacillus*.

In addition, the microbes of the genus *Thiobacillus* may be obligately autotrophic microbes or facultatively autotrophic microbes.

In addition, the obligately autotrophic microbes of the genus *Thiobacillus* may be one type of species selected from *Thiobacillus ferrooxidans*, *Thiobacillus albertis*, *Thiobacillus prosperus*, and *Thiobacillus thiooxidans* or a mixture of two or more types of species thereof.

In addition, the facultatively autotrophic microbes of the genus *Thiobacillus* may be one type of species selected from *Thiobacillus acidophilus* and *Thiobacillus cuprinus* or a mixture of two or more types of species thereof.

In the water toxicity detecting apparatus using sulfur particles according to the present invention, it is possible to detect electrical conductivity with high reproducibility and low error. In addition, since a range of the electrical conductivity is very wide (0~10000 μS/cm), it is possible to accurately detect generation of the sulfate ions.

In addition to a river, a lake, and a water supply source, the present invent can be used for detection of toxicity in a sewage water treatment plant or a waste water treatment plant. In addition, by reduction of the size of the sulfur particles, it is possible to miniaturize the apparatus.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
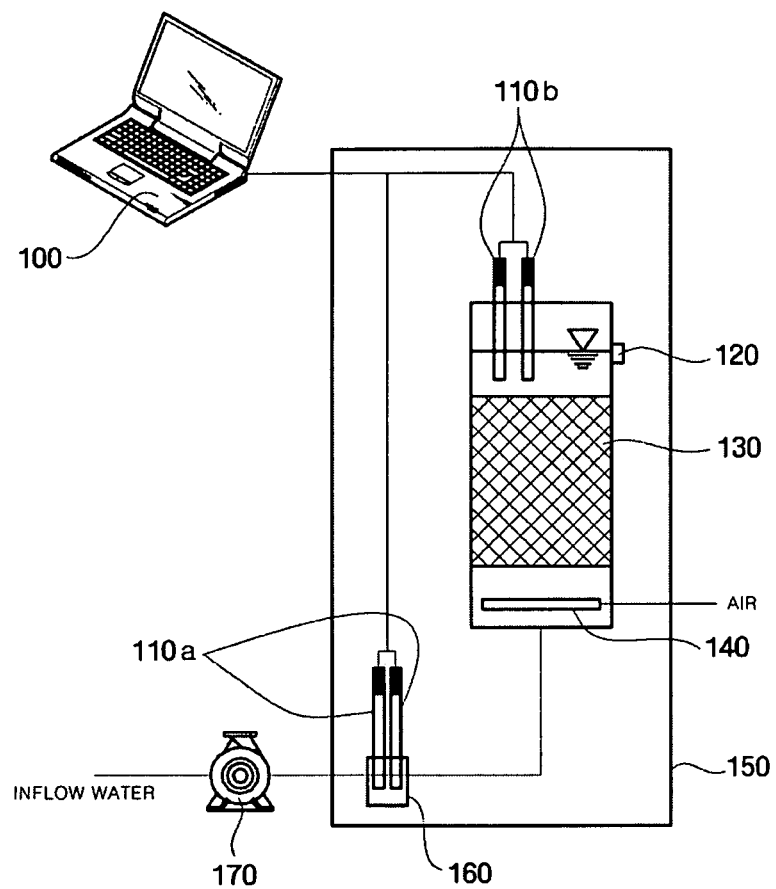
FIG. 1 is a schematic view showing a water toxicity detecting apparatus using sulfur particles according to an embodiment of the present invention.

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art. In the drawings, the thicknesses of layers and regions are exaggerated for clarity. Like reference numerals in the drawings denote like elements, and thus their description will be omitted.

FIG. 1 is a schematic view showing a water toxicity detecting apparatus using sulfur particles according to an embodiment of the present invention.

As shown in FIG. 1, the water toxicity detecting apparatus using sulfur particles according to the embodiment of the present invention includes: a central processing unit 100, a first detection unit 110a, a second detection unit 110b, a outlet 120, a reaction container 130, an air inlet 140, a thermostat unit 150, a water sample inlet 160, and a pump 170.

The central processing unit 100 stores data of changes in properties of an inflow water sample flown through the water sample inlet 160 and adjusts a pumping speed of the pump 170 provided to the water sample inlet 160 and a flow rate of an air flown into the reaction container.

The properties of the water sample include chemical, electrical, and physical properties. More specifically, the properties include pH and electrical conductivity.

The central processing unit 100 allows the first detection unit 110a and the second detection unit 110b to detect pH and electrical conductivity of the water samples in the inflow water and the reaction container 130 in a time interval of 0.5 to 20 minutes. Preferably, an alarm unit is cooperatively operated to automatically issue alarm when a ratio ($EC_{Difference}$ ratio) of difference between electrical conductivities detected by the first detection unit 110a and the second detection unit 110b is a predetermined value or less (for example, in a range of 0.3 to 0.8.

Preferably, as a means for introducing the water sample, the pump 170 is provided to the water sample inlet 160. In this case, air may be introduced together with the inflow water through the water sample inlet 160. Alternatively, the air may be introduced through the air inlet 140 into the reaction container 130, so that aeration can be directly performed in the reaction container.

After the test, the water sample is exhausted from the reaction container 130 through the outlet 120.

Preferably, the thermostat unit 150 is provided to maintain the reaction container 130 in which sulfur particles and oxygen are reacted by the microbes and the first detection unit 110a and the second detection unit 110b which detect pH and electrical conductivity in constant environments.

Preferably, as sulfur-oxidizing microbes used in the present invention, there are obligately autotrophic microbes, that is, obligately autotrophic color less sulfur bacteria such as *Thiobacillus ferrooxidans*, *Thiobacillus albertis*, *Thiobacillus prosperus*, and *Thiobacillus thiooxidans* and facultatively autotrophic microbes, that is, facultatively autotrophic color less sulfur bacteria such as *Thiobacillus acidophilus* and *Thiobacillus cuprinus*.

The microbes can be injected by using the aforementioned bacterial strain (pure culture).

Alternatively, the microbes are taken from a mixed culture in an environment where the sulfur-oxidizing microbes can be grown, and after that, the microbes are injected into the reaction container, so that microbes can be accommodated.

The mixed culture may be microbe-contained soil, sludge of river bottom, sludge of a waste water treatment plant, or the like. Preferably, in the injection, sufficient amounts of the pure culture or the mixed culture are introduced into the reaction container so as for a large number of the microbes to exist on surfaces of the sulfur particles. Preferably, aeration of oxygen is performed. Due the injection of the microbes, in most cases, the microbes are accommodated within one or two days, and the sulfur particles are oxidized into sulfates.

Figure 2:
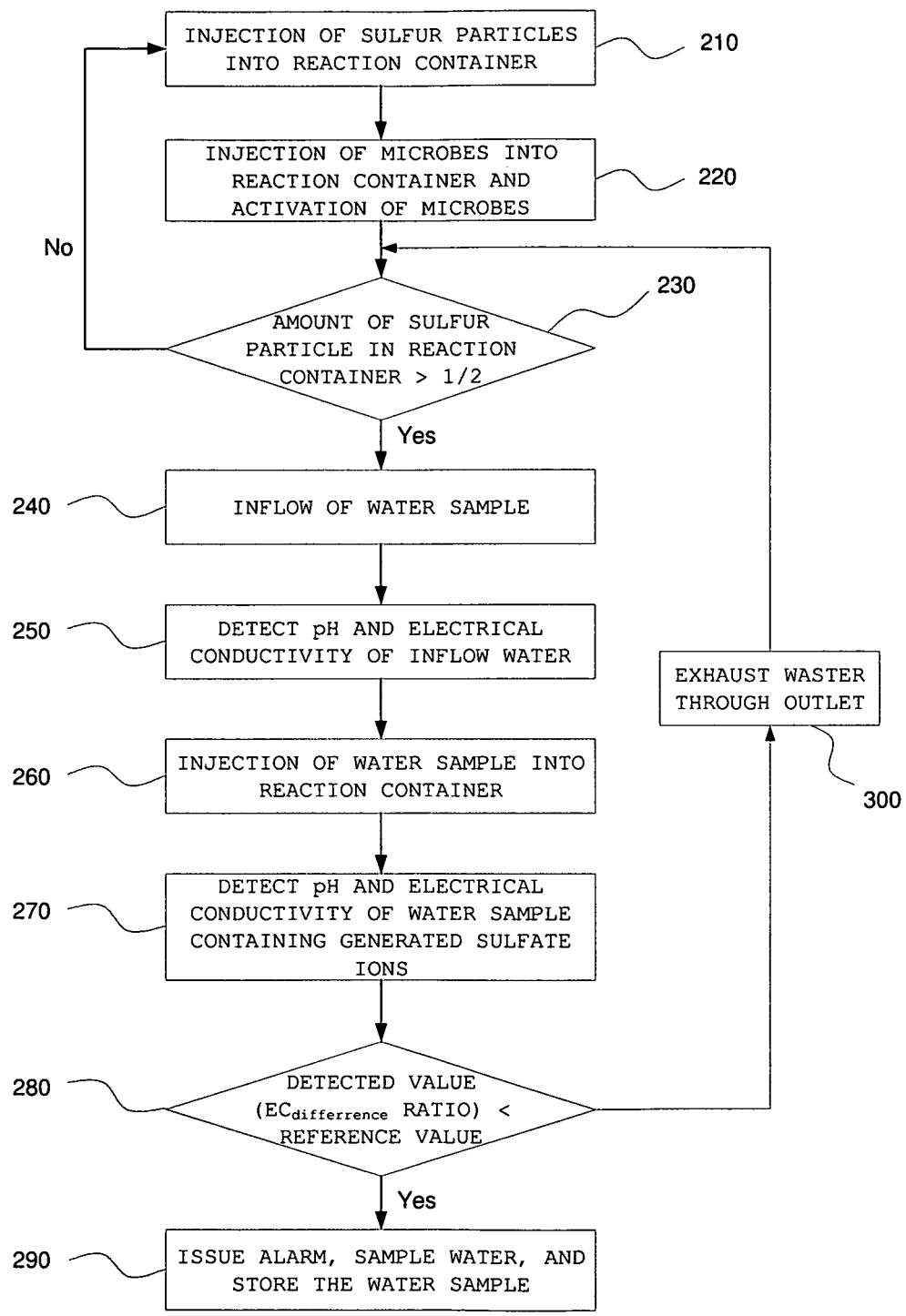
FIG. 2 is a flowchart showing a water toxicity detecting method using the water toxicity detecting apparatus using the sulfur particles shown in FIG. 1.

FIG. 2 is a flowchart showing a water toxicity detecting method using the water toxicity detecting apparatus using the sulfur particles shown in FIG. 1.

The water toxicity detecting method using the water toxicity detecting apparatus according to the embodiment of the present invention includes: a step 210 of introducing the sulfur particles into a reaction container; a step 220 of injecting microbes into the reaction container and activating the microbes; a step 230 of measuring the volume of sulfur particles in the reaction container and additionally introducing the sulfur particles if the volume of the sulfur particles is ½ or less of a total volume of the sulfur particles; a step 240 of flowing an external water sample through a water sample inlet; a step 250 of detecting pH and electrical conductivity of the inflow water sample flown through the water sample inlet; a step 260 of flowing the water sample into the reaction container; a step 270 of detecting pH and electrical conductivity of the water sample containing sulfate ions generated therein; a step 280 of comparing a ratio of difference between electrical conductivities detected from the inflow water sample flown through the water sample inlet and the water sample containing the generated sulfate ions with a predetermined value (reference value); a step 290 of issuing alarm and sampling the water when the ratio of difference between the electrical conductivities is less than the reference value in the step 280 of comparing; and a step 300 of exhausting the water sample from the reaction container when the ratio of difference between the electrical conductivities is not less than the reference value.

The sulfur particles in the reaction container 130 have a size of 0.01 mm to 6 mm. Preferably, in order to generate the sulfate ions in a shorter time, a surface area of the sulfur particles is increased by reducing the size of the sulfur particles.

As conditions for generating the sulfate ions, microbes as well as the sulfur particles may be injected into the reaction container 130.

In order to facilitate the generation and activation of the microbes, seeding is initially performed. AS a seeding substance, sewage containing various microbes or aerobic sludge of a sewage treatment plant is used.

An optimal temperature for the microbes is in a range of 30° C. to 35° C. If aeration is performed for 3 to 4 days, the sulfur particles are oxidized due to attachment of the microbes to the sulfur particles.

Preferably, as sulfur-oxidizing microbes used in the present invention, there are obligately autotrophic microbes, that is, obligately autotrophic color less sulfur bacteria such as *Thiobacillus ferrooxidans*, *Thiobacillus albertis*, *Thiobacillus prosperus*, and *Thiobacillus thiooxidans* and facultatively autotrophic microbes, that is, facultatively autotrophic color less sulfur bacteria such as *Thiobacillus acidophilus* and *Thiobacillus cuprinus*.

The microbes can be injected by using the aforementioned bacterial strain (pure culture). Alternatively, the microbes are taken from a mixed culture in an environment where the sulfur-oxidizing microbes can be grown, and after that, the microbes are injected into the reaction container 130, so that microbes can be accommodated.

The mixed culture may be microbe-contained soil, sludge of river bottom, sludge of a water treatment plant, or the like. Preferably, in the injection, sufficient amounts of the pure culture or the mixed culture are introduced into the reaction container 130 so as for a large number of the microbes to exist on surfaces of the sulfur particles. Preferably, aeration of oxygen is performed. Due the injection of the microbes, in most cases, the microbes are accommodated within one or two days, and the sulfur particles are oxidized into sulfates.

It can be understood by the ordinarily skilled in the art that the aforementioned anaerobic microbes are used. In addition, it can be understood by the ordinarily skilled in the art that sulfur-oxidizing microbes together with oxygen are preferably used even for a clean water or a water containing a slight amount of BOD.

As a reference, Table 1 shows classification of obligately autotrophic microbes and facultatively autotrophic microbes.

TABLE 1

| Classification | Carbon Source | | Energy Source | |
|---|---|---|---|---|
| | Inorganic Substance | Organic Substance | Inorganic Substance | Organic Substance |
| obligately autotrophic microbe | + | − | + | − |
| facultatively autotrophic microbe | + | + | + | + |
| inorganic-chemically heterotrophic microbe | − | + | + | + |
| heterotrophic microbe | − | + | − | + |

Now, processes of generating sulfate ions in the reaction container 130 of the water toxicity detecting apparatus using the sulfur particles according to the present invention will be described.

When the microbes attached around the sulfur particles are grown in the reaction container 130 of which conditions such as temperature is constant, the sulfur is oxidized at a constant speed. The following formula expresses a reaction of generation of sulfate ions and hydrogen ions in the processes.

$$S + H_2O + 1.5 O_2 \rightarrow SO_4^{2-} + 2H^+ \quad \Delta G^{\circ\prime} = -587.1 \text{ kJ/reaction}$$

Referring to the above formula, the sulfur particles react with the microbes, the inflow water, and the oxygen in the reaction container 130 to generate a predetermined amount of sulfate ions. In case of non-toxic outflow water, the amount of sulfate ions thereof is increased by a predetermined amount in comparison with the inflow water. Since a degree of alkali in a river water is generally low, pH of the outflow water is decreased in comparison with the inflow water.

However, in case of the inflow water containing toxic substances, a degree of activation of the microbes attached around the sulfur particles is lowered, so that the sulfur particles can not be oxidized. As a result, the sulfate cannot be generated, so that there is almost no difference between concentrations of sulfate ions of the inflow water and the outflow water.

In this case, the first detection unit 110a and the second detection unit 110b are preferably provided with a device for detecting pH of the inflow water and pH of the water sample in the reaction container 130. It is preferable that the pH of the inflow water is monitored by the device. Generally, the pH of the outflow water is decreased. However, if a buffer function of the inflow water is increased, the pH of the outflow water may not be decreased. Therefore, in the present invention, microbes which can be well grown in acid conditions are preferably used.

In general, the sulfate ions are analyzed by using instruments such as ion-chromatography. However, in the present invention, a change in concentration of the sulfate ions is indirectly measured through a measuring method using electric conductivity (EC).

According to the measuring method using the electrical conductivity, an amount of salts or ions dissolved in water can be estimated. Therefore, through the measuring method, a change in concentration of the sulfate ions can be measured based on the change in electrical conductivity.

The following formulas express the method of measuring the change in concentration of the sulfate ions base on the change in electrical conductivity.

$$EC_{outflow\ water} - EC_{inflow\ water} = EC_{Difference}$$

$$EC_{Difference}\ \text{Ratio} = EC_{Difference} / (EC_{Difference}\ \text{when } no\ \text{toxic}) = 0 \sim 1$$

The above formula expresses a ratio of the EC differences of the inflow water and the outflow water. If there is no toxicity in the inflow water, the ratio of the EC differences is approximate to 1. If there is a high toxicity in the inflow water, the ratio of the EC differences is approximate to 0. It is preferable that the electrical conductivity of the inflow water having no toxicity is periodically obtained by preparing a medium or river water without no electron acceptors and electron donors having no toxicity and measuring a difference of the electrical conductivity between the river water and the inflow water.

In case of a general inflow water, the pH and electrical conductivity are measured in a time interval of 1 to 5 minutes. In this case, a ratio of average values is obtained in a time interval of 30 minutes or 100 minutes by using the above formula.

The pH and electrical conductivity of the inflow water and the outflow water are detected in a predetermined time interval by using a two-line valve. In this case, since the pH may influence the result of the ratio of the EC differences, the ratio of the EC differences is collectively determined by monitoring the pH of the inflow water and the outflow water.

By repetition of the above method, a volume of the sulfur particles in the reaction container is decreased due to the oxidization thereof. When the volume of the sulfur particles in the reaction container is decreased down to ½ of total volume, a process of filling the reaction container with the sulfur particles is performed. At this time, the microbes need not to be additionally injected.

Now, the well-known principle of measuring the electrical conductivity is described as a reference.

Two electrodes, for example, Pt electrodes that are separated from each other by a separation distance of 1 cm are inserted into a water containing ions. A predetermined voltage is applied between the electrodes, and a generated current is measured so as to estimate electrical conductivity. The electrical conductivity of a pure water is approximate to 0 μS/cm. The electrical conductivity of river waters at upstream and downstream of Han River is in a range of 60 to 1300 μS/cm. The electrical conductivity of the river waters is mainly in a range of 100 to 300 μS/cm.

Since the method of measuring electrical conductivity has a small error and a wide range of value, the method is useful for detecting the generation of the sulfate ions.

In the present invention, the separation distance between the two electrodes needs not to be 1 cm. It is preferable that the separation distance between the two electrodes is reduced in a case where a higher value of the electrical conductivity is required.

In the water toxicity detecting apparatus using the sulfur particles, a hydraulic retention time (HRT) of the inflow water can be adjusted to be in a range of 1 minute to 30 minutes.

Rather than a large amount of air, a suitable amount of air is preferably injected according to circumstances. A smaller size of air bubble may be effective.

As the concentration of the sulfate ions generated from the reaction is higher and higher, an accurate determination of the toxicity can be more easily performed. For this reason, it is preferable that the air is continuously supplied to the reaction container. However, in a case where the air can be continuously flown from the atmosphere without aeration, the air needs not be continuously supplied.

Hereinafter, the present invention will be described based on the following embodiments, but the present invention is not limited thereto.

First Embodiment 1

Figure 3:
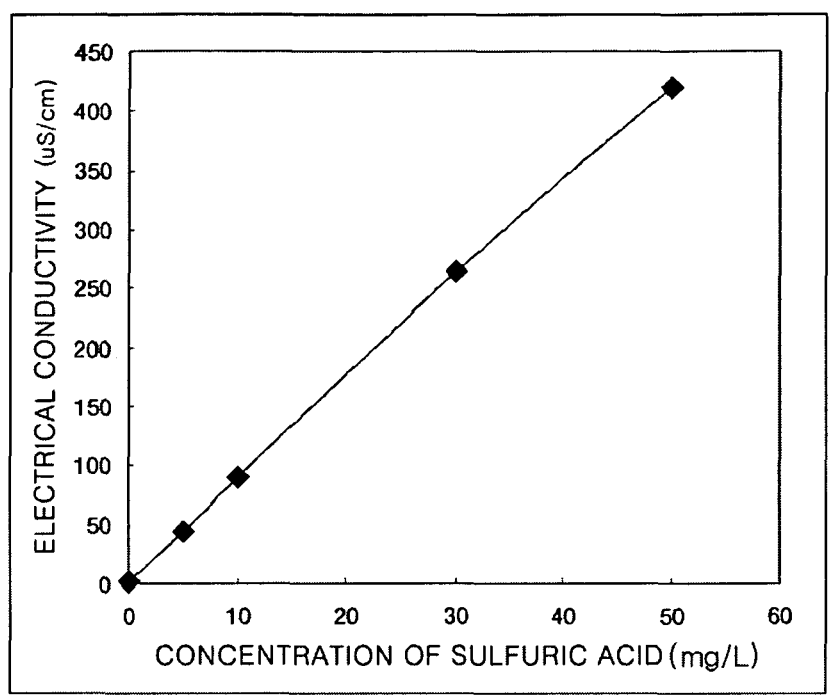
FIG. 3 is a graph showing a change in electrical conductivity according to a concentration of sulfuric acid detected by the water toxicity detecting apparatus using the sulfur particles shown in FIG. 1.

1000 gm/L of sulfuric acid is diluted by a pure water having no buffer function, so that 0, 5, 10, 30, and 50 mg/L of sulfuric acid are prepared so as to measure electrical conductivity. As shown in a result of the measurement of the electrical conductivity of FIG. 3, it can be seen that the electrical conductivity is proportional to a concentration of sulfuric acid.

If toxic substances are flown into the water sample in the reaction container, a degree of activation of the microbes is lowered due to the toxic substance, so that the concentration of sulfuric acid is decreased. Accordingly, the electrical conductivity is also decreased. In other words, the concentration of sulfuric acid can be estimated based on the result of measurement of the electrical conductivity of the water sample. Therefore, it can be determined whether or not a toxic substance is flown into the water sample.

Second Embodiment

An actual river water is used to be flown into the apparatus shown in FIG. 1. The reaction container is filled with a 30 mL of sulfur particles. A size of the sulfur particles is in a range of 1 mm to 4 mm, and a porosity thereof is 50%. A temperature is maintained at 30° C. While an empty bed contact time (EBCT) of the inflow water is changed among 7.1, 8.3, 10.0, 12.5, and 16.7 minutes, the pH and electrical conductivity of the inflow water and the outflow water are measured. The EBCT is calculated by dividing a volume (30 mL) of the sulfur particles with a flow rate. AS the air injection method, aeration is continuously performed.

The actual inflow river water is a Class-1 water, and the pH and electrical conductivity thereof are 7.8 and 282 μS/cm, respectively. It can be seen that, when the EBCT is about 17 minutes, a difference of electrical conductivity between the inflow water and the outflow water is 271 μS/cm. In addition, it can be seen that, as the EBCT is shorter and shorter, the difference of electrical conductivity is decreased.

Figure 4A:
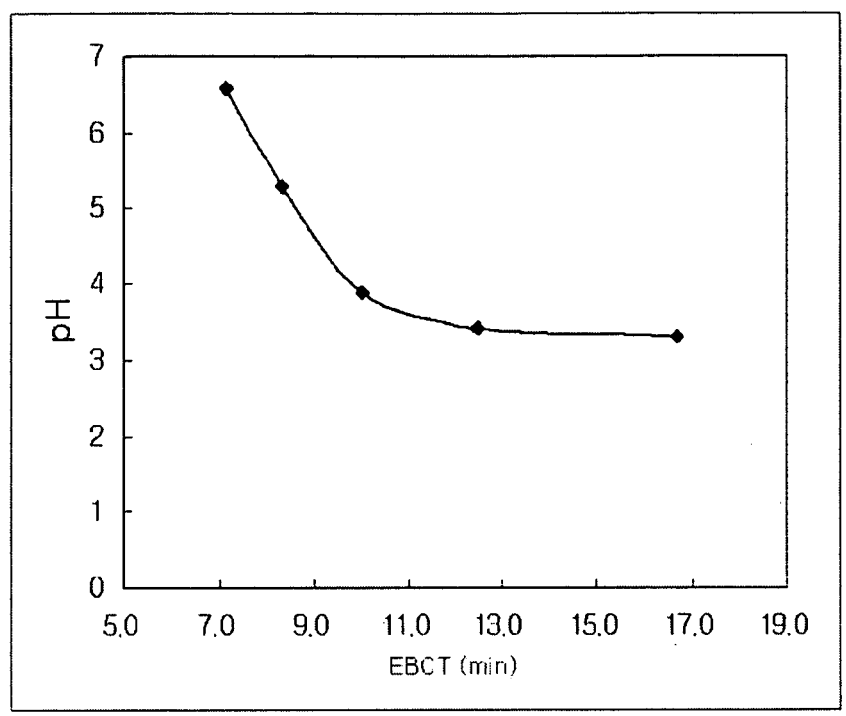
FIG. 4A is a graph showing a change in pH according to EBCT detected by the water toxicity detecting apparatus using the sulfur particles shown in FIG. 1.
Figure 4B:
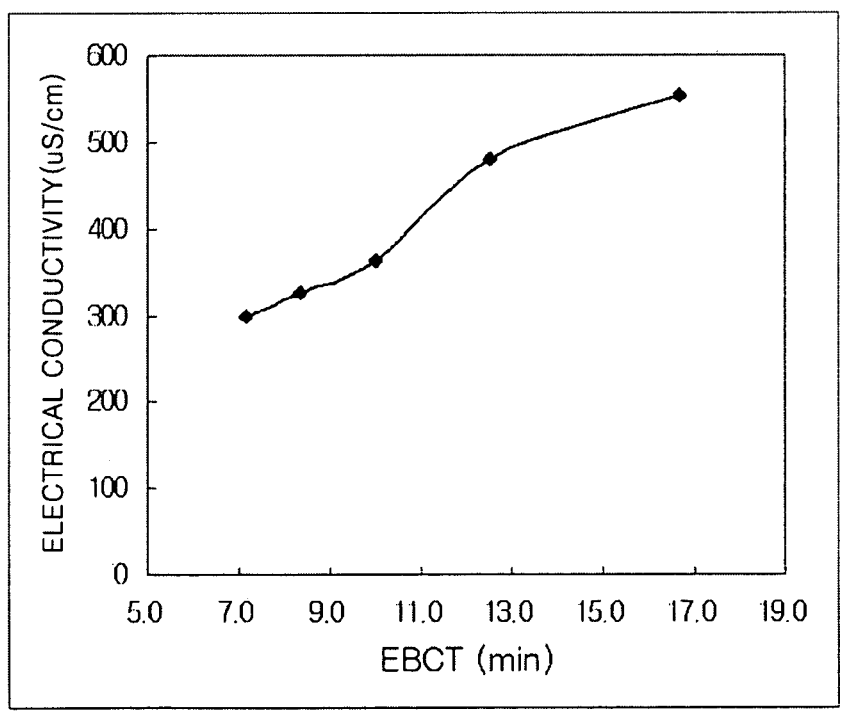
FIG. 4B is a graph showing a change in electrical conductivity according to EBCT detected by the water toxicity detecting apparatus using the sulfur particles shown in FIG. 1.

Referring to FIGS. 4A and 4B, when the EBCT is 17 minutes, the pH of the outflow water is 3.3, and as the EBCT is shortened toward 7 minutes, the pH of the outflow water is approximately equal to the pH of the inflow water. A sample containing a 30 ppm of hexavalent chrome as a test substance is flown with the EBCT of 17 minute. As a result, it can be seen that the $EC_{Difference}$ ratio is decreased down to 0.3, which corresponds to a case of issuing alarm.

As another example, an actual river water of 25 mL is flown into a batch-type toxicity monitoring apparatus. While air is continuously supplied, the pH and electrical conductivity are detected in a time interval of 5 minutes. In case of a river water having toxicity, it can be seen that, since a small amount of sulfate ions is generated, a rate of increment of electrical conductivity with respect to time as well as the electrical conductivity is low.

In case of livestock waste water, since it is used as nutrient sources for microbes or algae, the toxicity cannot be detected by using a biochemical toxicity monitoring apparatus. In general, the livestock waste water has electrical conductivity (EC) of 8,600 μS/cm, COD of 17,000 mg/L, ammonia of 2100 mgN/L, pH of 7.2, and TS (total solid) of 12,200 mg/L.

Such a livestock waste water having no toxicity has electrical conductivity of 8,600 μS/cm, and 1 μS/cm corresponds to COD of 2 mg and N of 0.3 mg. Therefore, releasing of the livestock waste water leads to an increase in electrical conductivity. Accordingly, the releasing or a degree of dilution of the livestock waste water can be determined through the apparatus according to the present invention. For example, if the electrical conductivity of the inflow river waster is three times daily average of electrical conductivity, alarm is designed to be issued.

While the present invention has been particularly shown and described with reference to exemplary embodiments thereof, it will be understood by those skilled in the art that various changes in form and details may be made therein without departing from the spirit and scope of the invention. The exemplary embodiments should be considered in descriptive sense only and not for purposes of limitation. Therefore, the scope of the invention is not limited by the detailed description of the invention, and all differences within the scope will be construed as being included in the present invention.

What is claimed is:

1. A water toxicity detecting apparatus using sulfur particles comprising:
    a single reaction container containing unrestrained injected microbes accreted on surfaces of externally-supplied sulfur particles, in which the externally-supplied sulfur particles and oxygen are reacted to form sulfate ions by the microbes;
    a water sample inlet through which an inflow water sample is flown into the single reaction container;
    an air inlet through which an air is flown into the single reaction container;
    a first detection unit which is configured to detect only pH and electrical conductivity of the inflow water sample flown through the water sample inlet;
    a second detection unit which is configured to detect only pH and electrical conductivity of a water sample containing the sulfate ions generated in the single reaction container;
    a central processing unit which stores data of the ph and electrical conductivity of the inflow water sample flown through the water sample inlet, adjusts a pumping speed of a pump provided to the water sample inlet and a flow rate of the air, and compares data of the first detection unit with data of the second detection unit to determine presence of toxicity of the water sample via only differences in pH and electrical conductivity resulting from differences in sulfate ion concentration from the first detection unit and the second detection unit; and
    an outlet through which an after-toxicity-test water sample is exhausted from the single reaction container.

2. The water toxicity detecting apparatus of claim 1, further comprising:
    thermostat unit which maintain the reaction container at a constant temperature;
    an alarm unit which issues alarm when a detected value of the electrical conductivity in the reaction container deviates from a reference value; and
    water sampling unit which samples the water for accurate analysis at the same time of the issuing of alarm and stores the sample.

3. The water toxicity detecting apparatus of claim 1, wherein the reaction container is of a continuous type or a batch type.

4. The water toxicity detecting apparatus of claim 1, further comprising a pump which is provided to the water sample inlet to introduce a river water.

5. The water toxicity detecting apparatus of claim 1, wherein the microbes belong to the genus *Thiobacillus*.

6. The water toxicity detecting apparatus of claim 5, wherein the microbes of the genus *Thiobacillus* are obligately autotrophic microbes or facultatively autotrophic microbes.

7. The water toxicity detecting apparatus of claim 6, wherein the obligately autotrophic microbes of the genus *Thiobacillus* are one type of species selected from *Thiobacillus ferrooxidans, Thiobacillus albertis, Thiobacillus prosperus*, and *Thiobacillus thiooxidans* or a mixture of two or more types of species thereof.

8. The water toxicity detecting apparatus of claim 6, wherein the facultatively autotrophic microbes of the genus *Thiobacillus* are one type of species selected from *Thiobacillus acidophilus* and *Thiobacillus cuprinus* or a mixture of two or more types of species thereof.

9. A water toxicity detecting method using sulfur particles, comprising:
    introducing the sulfur particles into a single reaction container;
    injecting unrestrained microbes into the reaction container and activating the microbes, the microbes are accreted on surfaces of the sulfur particles;
    flowing a water sample into the single reaction container;
    supplying air to the single reaction container;
    detecting pH and electrical conductivity of an inflow water sample flown through a water sample inlet;
    detecting pH and electrical conductivity of a water sample containing sulfate ions generated in the single reaction container;
    storing data of the pH and electrical conductivity of the inflow water sample flown through the water sample inlet and adjusting a pumping speed of a pump provided to the water sample inlet and a flow rate of the air supplied to the single reaction container; and
    determining presence of toxicity of the water sample based on data of changes in only pH and electrical conductivity between the inflow water sample flown through the water sample inlet and the water sample containing sulfate ions generated in the single reaction container.

10. The water toxicity detecting method of claim 9, further comprising:
    comparing the detected value of electrical conductivity with a reference value and issuing alarm of abnormal water quality if the detected value is less than the reference value; and
    sampling the water for accurate analysis at the same time of the issuing of alarm and storing the sample.

11. The water toxicity detecting method of claim 9, wherein the microbes belong to the genus *Thiobacillus*.

12. The water toxicity detecting method of claim 11, wherein the microbes of the genus *Thiobacillus* are obligately autotrophic microbes or facultatively autotrophic microbes.

13. The water toxicity detecting method of claim 12, wherein the obligately autotrophic microbes of the genus *Thiobacillus* are one type of species selected from *Thiobacillus ferrooxidans, Thiobacillus albertis, Thiobacillus prosperus*, and *Thiobacillus thiooxidans* or a mixture of two or more types of species thereof.

14. The water toxicity detecting method of claim 12, wherein the facultatively autotrophic microbes of the genus *Thiobacillus* are one type of species selected from *Thiobacillus acidophilus* and *Thiobacillus cuprinus* or a mixture of two or more types of species thereof.

* * * * *